(12) United States Patent
Hintzer et al.

(10) Patent No.: US 10,099,982 B2
(45) Date of Patent: Oct. 16, 2018

(54) METHODS OF MAKING HALOGENATED PARTIALLY FLUORINATED COMPOUNDS

(71) Applicant: 3M INNOVATIVE PROPERTIES COMPANY, St. Paul, MN (US)

(72) Inventors: Klaus Hintzer, Kastl (DE); Markus E. Hirschberg, Burgkirchen (DE); Kai Helmut Lochhaas, Neuotting (DE); Oleg Shyshkov, Burgkirchen (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 15/529,116

(22) PCT Filed: Dec. 4, 2015

(86) PCT No.: PCT/US2015/063947
§ 371 (c)(1),
(2) Date: May 24, 2017

(87) PCT Pub. No.: WO2016/105907
PCT Pub. Date: Jun. 30, 2016

(65) Prior Publication Data
US 2017/0283351 A1     Oct. 5, 2017

Related U.S. Application Data

(60) Provisional application No. 62/095,300, filed on Dec. 22, 2014.

(51) Int. Cl.
| | |
|---|---|
| C07C 43/12 | (2006.01) |
| C07C 17/087 | (2006.01) |
| C07C 41/20 | (2006.01) |
| C07C 17/20 | (2006.01) |
| C07C 41/18 | (2006.01) |
| C07C 17/093 | (2006.01) |
| C07C 19/16 | (2006.01) |
| C07C 21/18 | (2006.01) |

(52) U.S. Cl.
CPC .......... *C07C 43/126* (2013.01); *C07C 17/087* (2013.01); *C07C 17/093* (2013.01); *C07C 17/208* (2013.01); *C07C 19/16* (2013.01); *C07C 21/18* (2013.01); *C07C 41/18* (2013.01); *C07C 41/20* (2013.01)

(58) Field of Classification Search
CPC ..... C07C 43/126; C07C 41/20; C07C 17/087; C07C 17/208; C07C 17/206
See application file for complete search history.

(56) References Cited

U.S. PATENT DOCUMENTS

| 5,504,248 A | 4/1996 | Krusic |
| 2010/0261869 A1 | 10/2010 | Horiuti |
| 2011/0245520 A1 | 10/2011 | Zipplies |

FOREIGN PATENT DOCUMENTS

| EP | 1 457 477 | 9/2004 |
| GB | 1012797 | 12/1965 |
| RU | 2064915 | 8/1996 |
| WO | WO 1996-03358 | 2/1996 |
| WO | WO 2014/062469 | 4/2014 |

OTHER PUBLICATIONS

Knunyants, "Addition of hydrogen halides to fluoro olefins", Bulletin of the Academy Sciences of the USSR, 1960, vol. 9, pp. 1568-1569.
Park, "The addition of hydrogen bromide to fluorinated olefins", J. Am. Chem. Soc., 1949, vol. 71, pp. 2339-2340.
Stacey, "The Radical Addition of Hydrogen Bromide to Hexafluoropropene", Contribution No. 792 from the Central Research Department, 1962, vol. 27, pp. 4089-4090.
Wlassics, "Perfluoro Allyl Fluorosulfate (FAFS): A Versatile Building Block for New Fluoroallylic Compounds", Molecules, 2011, vol. 16, pp. 6512-6540.
Yang, "Diiododifluoromethane: an excellent telegen for the preparation of 1,3-diiodofluoropropane derivaties", Journal of Fluorine Chemistry, 2000, vol. 102, pp. 239-241.
Yang, "Ring-Opening Reaction of Fluorocyclopropanes with Halogens: A General and Useful Route to 1,3-Dihalofluoropropane Derivatives", J. Am. Chem. Soc., 1995, vol. 117, pp. 5397-5398.
Yang, "Environmentally Benign Process for Making Useful Fluorocarbons: Nickel- or Copper(I) Iodide-Catalyzed Reaction of Highly Fluorinated Epoxides with Halogens in the Absence of Solvent and Thermal Addition of $CF_2I_2$ to Olefins$^§$", J. Org. Chem., 2004, vol. 69, pp. 2394-2403.
Yang, "Preparation of Highly Fluorinated Cyclopropanes and Ring-Opening Reactions with Halogens", J. Org. Chem., 2003, vol. 68, pp. 4410-4416.
International Search Report for International Application No. PCT/US2015/063947 dated Feb. 16, 2016, 4 pages.
Haszeldine, "715. The Addition of Free Radicals to Unsaturated Systems. Part IV. The Direction of Radical Addition to Hexafluoropropene," Journal of the Chemical Society, Jan. 1, 1953, pp. 3559-3564.
Norris, et al., "The Origin of the Anisochronism of Geminal Groups in Conformationally Mobile Systems. II. Intrinsic and Conformational Contributions in Asymmetric Fluoroethanes," Journal of the American Chemical Society, vol. 95. No. 1, Jan. 1, 1973, pp. 182-190.

*Primary Examiner* — Rosalynd A Keys
(74) *Attorney, Agent, or Firm* — Julie Lapos-Kuchar

(57) ABSTRACT

Described herein is method of making a halogenated partially fluorinated compound, comprising: (a) providing a compound having the following structure of formula (I): $R_f$—CF=CXY wherein X and Y are independently selected from F and Cl; wherein $R_f$ is a fluorinated monovalent group comprising 1 to 10 carbon atoms; (b) contacting the compound with at least one of (i) an iodine or bromine containing salt in the presence of an acid; and (ii) aqueous solution of HZ wherein Z is selected from I and Br to form the halogenated partially fluorinated compound of the formula (II): $R'_f$—CFH—CXYZ wherein X and Y are independently selected from F and Cl; Z is selected from I and Br; and $R'_f$ is a fluorinated monovalent group comprising 1 to 10 carbon atoms.

15 Claims, No Drawings

METHODS OF MAKING HALOGENATED PARTIALLY FLUORINATED COMPOUNDS

CROSS REFERECE TO RELATED APPLICTIONS

This application is a national stage filing under 35 U.S.C. 371 of PCT/US2015/063947, filed Dec. 4, 2015, which claims the benefit of U.S. Application No. 62/095,300, filed Dec. 22, 2014, the disclosure of which is incorporated by reference in its/their entirety herein.

TECHNICAL FIELD

Methods of making halogenated partially fluorinated compounds from a perhalogenated terminal olefin are disclosed.

BACKGROUND

Bromine/iodine containing compounds are key materials for producing peroxide curable elastomers. They are used as chain transfer agents (CTA) and/or as cure site monomers (CSM) in polymer synthesis. For example, diiodoperfluorobutane [I(CF$_2$)$_4$I] is a popular chain transfer agent.

Typically, α,ω-diiodo (per)fluoroalkanes are prepared by radical reaction of iodine with a fluoroolefin, reaction of ICF$_2$I with a (fluoro)olefin, telomerization of a (fluoro)olefin with shorter-chained α,ω-diiodo fluoroalkanes, and coupling reactions of diiodofluoroalkanes.

Partially fluorinated α,ω-diiodo fluoroalkanes, such as I—CF$_2$—CFH—CF$_2$—I have been prepared by reaction of pentafluorocyclopropane (c-C$_3$F$_5$H) with iodine, as described in *J. Am. Chem. Soc.* 1995, 117, 5397-5398; or by the reaction of CF$_2$I$_2$ with trifluoroethylene (CF$_2$=CHF), as described in *J. Org. Chem.* 2004, 69, 2394-2403.

SUMMARY

There is a desire for alternative methods of making partially fluorinated compounds, which may be simpler, use more readily available starting materials, and/or are more cost effective than current manufacturing processes.

In one aspect, a method of making a partially fluorinated halogenated compound is described comprising:
(a) providing a compound having the following structure of formula (I):

R$_f$—CF=CXY wherein X and Y are independently selected from F and Cl; wherein R$_f$ is a fluorinated monovalent group comprising 1 to 10 carbon atoms;
(b) contacting the compound with at least one of
(i) an iodine or bromine containing salt in the presence of an acid; and
(ii) aqueous solution of HZ wherein Z is selected from I and Br to form the halogenated partially fluorinated compound of the formula (II):

R'$_f$—CFH—CXYZ wherein X and Y are independently selected from F and Cl; Z is selected from I and Br; and R'$_f$ is a fluorinated monovalent group comprising 1 to 10 carbon atoms.

In another aspect, novel halogenated partially fluorinated compounds are described.

The above summary is not intended to describe each embodiment. The details of one or more embodiments of the invention are also set forth in the description below. Other features, objects, and advantages will be apparent from the description and from the claims.

DETAILED DESCRIPTION

As used herein, the term
"a", "an", and "the" are used interchangeably and mean one or more; and
"and/or" is used to indicate one or both stated cases may occur, for example A and/or B includes, (A and B) and (A or B).

Also herein, recitation of ranges by endpoints includes all numbers subsumed within that range (e.g., 1 to 10 includes 1.4, 1.9, 2.33, 5.75, 9.98, etc.).

Also herein, recitation of "at least one" includes all numbers of one and greater (e.g., at least 2, at least 4, at least 6, at least 8, at least 10, at least 25, at least 50, at least 100, etc.).

The present disclosure is directed toward the addition reaction of an iodine or bromine containing compound to a terminal double bond containing compound of the formula (I)

$$R_f\text{—CF=CXY} \quad (I)$$

wherein X and Y are independently selected from F and Cl; wherein R$_f$ is a fluorinated monovalent group comprising 1 to 10 carbon atoms.

R$_f$ may be partially fluorinated (comprising at least one carbon-hydrogen bond and at least one carbon-fluorine bond) or perfluorinated (comprising at least one carbon-fluorine bond and no carbon-hydrogen bonds). R$_f$ may be linear, branched, or cyclic. R$_f$ may be saturated or unsaturated, optionally comprising at least one catenated O, S, and/or N (e.g., an ether linkage). In some embodiments, R$_f$ comprises at least one halogen selected from Cl, Br, and I.

In one embodiment, R$_f$ comprises a functional group selected from a sulfate, a carboxylate, a nitrile, and a sulfonate.

In one embodiment, R$_f$ is selected from —CF$_2$—O—SO$_2$F; —CF$_2$—I; —CF$_2$—Br; —O—(CF$_2$)$_a$—F; —O—(CF$_2$)$_a$—I; —O—(CF$_2$)$_a$—Br; —O—(CF$_2$)$_b$—O—CF=CXY wherein X and Y are independently selected from F and Cl; a is an integer from 1-10; and b is an integer from 2-4.

Exemplary, compounds of formula (I) have the structure:
X'—CF$_2$—CF=CF$_2$, CF$_3$—O—CF=CF$_2$, C$_3$F$_7$—O—CF=CF$_2$, CF$_3$CF$_2$CF$_2$—O—CF(CF$_3$)—CF$_2$—O—CF=CF$_2$, X'—(CF$_2$)$_{1-4}$—CF=CF$_2$, CF$_3$—O—(CF$_2$)$_3$—O—CF=CF$_2$, CF$_2$=CF—O—(CF$_2$)$_{2-4}$—O—CF=CF$_2$, X'—CF$_2$—CF$_2$—O—(CF$_2$)$_{2-4}$—O—CF=CF$_2$, CF$_2$=CF—O—(CF$_2$)$_{2-4}$—O—CF$_2$—CF=CF$_2$, CF$_2$=CF—CF$_2$—O—(CF$_2$)$_{2-4}$—O—CF$_2$—CF=CF$_2$, X'—CF$_2$—CF$_2$—O—(CF$_2$)$_{2-4}$—O—CF$_2$CF=CF$_2$, X'—CF$_2$—CF$_2$—O—CF=CF$_2$, X'—CF$_2$—CF$_2$—O—CF$_2$—CF=CF$_2$, X'—CF(CF$_3$)—CF$_2$—O—CF=CF$_2$, X'—CF(CF$_3$)—CF$_2$—O—CF$_2$—CF=CF$_2$, X'—CF$_2$—CF$_2$—(O—CF(CF$_3$)—CF$_2$)$_{1-2}$—O—CF=CF$_2$, X'—CF$_2$—CF$_2$—(O—CF(CF$_3$)—CF$_2$)$_{1-2}$—O—CF$_2$—CF=CF$_2$, X'—CF$_2$—CF$_2$—CF$_2$—O—CF=CF$_2$, X'—CF$_2$—CF$_2$—CF$_2$—O—CF$_2$—CF=CF$_2$, X'—CF$_2$—CF$_2$—CF$_2$—(O—CF(CF$_3$)—CF$_2$)$_{1-2}$—O—CF=CF$_2$, X'—CF$_2$—CF$_2$—CF$_2$—(O—CF(CF$_3$)—CF$_2$)$_{1-2}$—O—CF$_2$—CF=CF$_2$, or X'—CF$_2$—CF$_2$—O—(CF$_2$)$_2$—(O—CF(CF$_3$)CF$_2$)$_{1-2}$—O—CF$_2$=CF$_2$ wherein X' is selected from Br, I, C(O)X", and SO$_2$X" wherein X" is selected from F, Cl, OH, and salts thereof.

It has been discovered that by reacting the compound of formula (I) with either (i) an iodine or bromine containing salt in the presence of an acid or (ii) an aqueous solution of HZ wherein Z is selected from I and Br, the compound of formula (I) undergoes an addition reaction forming a halogenated partially fluorinated compound of formula II

$$R'_f\text{—CFH—CXYZ} \quad \text{(II)}$$

wherein X and Y are the same as above, Z is selected from I and Br, and $R'_f$ is a monovalent fluorinated group.

In one embodiment, $R'_f$ is the same as $R_f$ in the starting material. In another embodiment $R'_f$ is different from $R_f$.

Exemplary, compounds of formula (II) have the structure:
X'—$CF_2$—CFH—$CF_2$—Z, $CF_3$—O—CFH—$CF_2$—Z, $C_3F_7$—O—CFH—$CF_2$—Z, $CF_3CF_2CF_2$—O—CF($CF_3$)—$CF_2$—O—CFH—$CF_2$—Z, X'—$(CF_2)_{1-4}$—CFH—$CF_2$—Z, $CF_3$—O—$(CF_2)_3$—O—CFH—$CF_2$—Z, Z—$CF_2$—CFH—O—$(CF_2)_{2-4}$—O—CF=$CF_2$, Z—$CF_2$—CFH—O—$(CF_2)_{2-4}$—O—CFH—$CF_2$—Z, Z—$CF_2$—CFH—O—$(CF_2)_{2-4}$—O—$CF_2$—CF=$CF_2$, Z—$CF_2$—CFH—O—$(CF_2)_{2-4}$—O—$CF_2$—CFH—$CF_2$—Z, $CF_2$=CF—O—$(CF_2)_{2-4}$—O—$CF_2$—CFH—$CF_2$—Z, Z—$CF_2$—CFH—$CF_2$—O—$(CF_2)_{2-4}$—O—$CF_2$=$CF_2$, Z—$CF_2$—CFH—$CF_2$—O—$(CF_2)_{2-4}$—O—$CF_2$—CFH—$CF_2$—Z, X'—$CF_2$—$CF_2$—O—$(CF_2)_{2-4}$—O—$CF_2$CFH—$CF_2$—Z, X'—$CF_2$—$CF_2$—O—CFH—$CF_2$—Z, X'—$CF_2$—$CF_2$—O—$CF_2$—CFH—$CF_2$—Z, X'—CF($CF_3$)—$CF_2$—O—CFH—$CF_2$—Z, X'—CF($CF_3$)—$CF_2$—O—$CF_2$—CFH—$CF_2$—Z, X'—$CF_2$—$CF_2$—(O—CF($CF_3$)—$CF_2$)$_{1-2}$—O—CFH—$CF_2$—Z, X'—$CF_2$—$CF_2$—(O—CF($CF_3$)—$CF_2$)$_{1-2}$—O—$CF_2$—CFH—$CF_2$—Z, X'—$CF_2$—$CF_2$—$CF_2$—O—CFH—$CF_2$—Z, X'—$CF_2$—$CF_2$—$CF_2$—O—$CF_2$—CFH—$CF_2$—Z, X'—$CF_2$—$CF_2$—$CF_2$—(O—CF($CF_3$)—$CF_2$)$_{1-2}$—O—CFH—$CF_2$—Z, X'—$CF_2$—$CF_2$—$CF_2$—(O—CF($CF_3$)—$CF_2$)$_{1-2}$—O—$CF_2$—CFH—$CF_2$—Z, X'—$CF_2$—$CF_2$—O—$(CF_2)_2$—(O—CF($CF_3$)$CF_2$)$_{1-2}$—O—CFH—$CF_2$—Z wherein Z is Br and I; X' is selected from Br, I, C(O)X", and $SO_2$X"

wherein X" is selected from F, Cl, OH, and salts thereof. Exemplary salts of the C(O)OH include for example, ammonium salts, alkali and alkaline earth metal salts, such as C(O)ONa.

In one embodiment, the compound of formula (I) is reacted with an iodine or bromine containing salt in the presence of an acid.

The iodine or bromine containing salt is of the formula $Z_iM^{+i}$, where Z is selected from I and Br, and M is a counter ion with a valency of i in the range of 1 to 4, preferably i is 1 to 2. In one embodiment, the counter ion is organic, such as an alkylammonium (e.g., tetramethylammonium, terabutylammonium, etc.). In another embodiment, the counter ion is inorganic, such as an ammonium, or a metal, such as alkali metal (e.g., Na, K, Li, etc.) or alkaline earth metal (e.g., Mg, Ca, etc.).

Typically the molar ratio of the salt to formula (I) is 0.5:1 to 10:1, preferably 1:1 to 5:1.

An acid is used to favor the addition reaction of the halogenide to the terminal olefin. Generally the lower the pKa (the stronger the acid) the better the yield for the addition reaction. In one embodiment the acid has a pKa of no more than 4.8 at 25° C., or even no more than 2. Exemplary acids include sulfonic acids (e.g. trifluoromethanesulfonic acid) and carboxylic acids (e.g. acetic acid and trifluoroacetic acid), or mixtures thereof. The acids may be diluted with water to any concentration, preferably the acids or mixtures thereof are used in the absence of water.

The reaction of the iodine or bromine containing salt with the compound of formula (I) may occur in an aqueous solution or a non-aqueous solution.

Exemplary solvents that are preferably used are non-reactive organic solvents, such as those which have a boiling point up to 275° C. (e.g. triglyme and tetraglyme), preferably those having a boiling point up to 170° C. (e.g. $CH_3CN$, tetrahydrofuran, propionitrile, monoglyme, diglyme) or mixtures thereof. Exemplary solvents include: acetonitrile, diglyme, monoglyme, propionitrile, triglyme, tetraglyme, tetrahydrofuran, water, and mixtures thereof.

In one embodiment, the reaction of the iodine or bromine containing salt with the compound of formula (I) may occur at pressures from at least ambient (1 bar), 3 bar, or even 5 bar to pressures no higher than 10 bar, 15 bar, or even 20 bar. In one embodiment, the reaction of the iodine or bromine containing salt with the compound of formula (I) may occur at temperatures of at least −10° C., 0° C., 20° C., 25° C., 30° C., 40° C., or even 50° C.; and at most 275° C., 250° C., 220° C., 200° C., 180° C., 150° C., 120° C., 110° C., or even 100° C.

In another embodiment, the compound of formula (I) is reacted with an aqueous solution comprising HZ wherein Z is selected from I and Br.

In one embodiment, the molar ratio of HZ to formula (I) is 0.5:1 to 10:1, preferably 1:1 to 5:1.

In one embodiment, the reaction of HZ with the compound of formula (I) may occur at pressures from at least ambient (1 bar), 3 bar, or even 5 bar to pressures no higher than 10 bar, 15 bar, or even 20 bar. In one embodiment, the reaction of HZ with compound of formula (I) may occur at temperatures of at least −10° C., 0° C., 20° C., 25° C., 30° C., 40° C., or even 50° C.; and at most 275° C., 250° C., 220° C., 200° C., 180° C., 150° C., 120° C., 110° C., or even 100° C.

In one embodiment, the reaction of HZ with the compound of formula (I) can be conducted in the presence of cosolvents. Exemplary cosolvents that are preferably used are non-reactive organic solvents, as those which have a boiling point up to 275° C. (e.g. triglyme and tetraglyme), preferably those having a boiling point up to 170° C. (e.g. $CH_3CN$, tetrahydrofuran, propionitrile, monoglyme, diglyme) or mixtures thereof. Exemplary solvents include: acetonitrile, diglyme, monoglyme, propionitrile, triglyme, tetraglyme, tetrahydrofuran, water, and mixtures thereof.

The reactions described above involve the addition of the HBr an HI group across the double bond of formula (I), thus, the $R_f$ group should remain unchanged in the product (i.e., $R'_f$ in formula (II)). However, as mentioned above, in one embodiment, $R'_f$ is different from $R_f$. Such differences may be due to the reaction of the iodine or bromine containing compounds (i.e., the iodine or bromine salts in the presence of an acid or HZ with Z=I, Br) with reactive groups located in the $R_f$ group (e.g. carboxylate, nitrile, or unsaturated groups).

When the compound of formula (I) comprises two terminal double bonds (such as divinyl ethers of the formula $CF_2$=CF—O—$(CF_2)_{2-4}$—O—CF=$CF_2$ or $CF_2$=CF—O—CF=$CF_2$), the amount of compound according to formula (I) to the amount of the iodine or bromine containing compounds (i.e., the iodine or bromine salts in the presence of an acid or HZ with Z=I, Br) can be adjusted to favor the reaction of one or both terminal double bonds.

As will be shown in the examples, the preparation of I—$CF_2$—CFH—$CF_2$—I using the methods disclosed herein can occur in either a two-step or a one-step synthesis. For example, perfluoroallyl fluorosulfate ($CF_2$=CF—$CF_2$—

O—SO$_2$F) can be reacted in a first step with an iodine containing salt via nucleophilic substitution reaction, followed by a second step, wherein the CF$_2$=CF—CF$_2$—I is reacted with an iodine containing salt in the presence of an acid. Alternatively, the perfluoroallyl fluorosulfate can directly be reacted with an iodine containing salt in the presence of an acid.

Further, in another embodiment, the halogenated partially fluorinated compound of formula (II) can be reacted with a hydrocarbon olefin such as ethylene to elongate the halogenated partially fluorinated compound, adding, for example, a —CH$_2$—CH$_2$—group. This group on the elongated halogenated partially fluorinated compound can then be reduced to form a partially fluorinated compound according to formula (III):

R''—CFH—CF$_2$—CH=CH$_2$ wherein R'' is selected from X'—CF$_2$—, CH$_2$=CH—CF$_2$—, CF$_3$O—, CF$_3$CF$_2$CF$_2$—O—, or CF$_3$—O—(CF$_2$)$_3$—O—, wherein X' is selected from Br, I, C(O)X'', and SO$_2$X'' wherein X'' is selected from F, Cl, OH, and salts thereof Such insertions of the hydrocarbon olefin into the halogenated partially fluorinated compounds of formula (II) could be conducted by known methods in the absence or in the presence of a radical initiator (e.g. di-tert-butyl peroxide, azobisisobutyronitrile), in the absence or in the presence of a catalyst (e.g. Ni, Cu, Fe, CuCl/CH$_3$CN, P(OEt)$_3$, Ru/C, Pt/C, Ag/Al$_2$O$_3$, Ni(CO)$_2$(PPh$_3$)$_2$, W(CO)$_5$P(OEt)$_3$, Mo(CO)$_5$(PPh$_3$), where Et is ethyl and Ph is phenyl). Exemplary reaction times are from at least 2, 3, 6, or even 10 hrs up to 12, 15, or even 24 hrs or more. Exemplary reaction temperatures are from at least 30, 50, 75, 100, or even 150° C. up to 175, 200, 225, or even 250° C. Typically the reaction is conducted in a steel or hastelloy autoclave.

Subsequently, the corresponding ethylene elongated compound can be reduced to a double bond by known methods (e.g. via KOH/phase transfer catalysts, KOH/EtOH, trialkylamines, Zn/DMF at temperatures ranging from at least 0, 25, 50, 75 or even 100° C. up to 175, 200, 225, or even 250° C.).

The compounds according to formulas (II) and (III) can be used, for example, as starting materials or building blocks in chemical synthesis, and/or as a chain transfer agents and/or cure site monomers in a fluoropolymer polymerization.

The reactions disclosed herein involve contacting the compound of formula (I) with an iodide or bromide ion in the presence of an acid. Advantageously, the reactions can be conducted at mild pressures and temperatures (for example, ambient pressure at 100° C.). Advantageously, in one embodiment, the resulting products can be isolated from the reaction by phase separation. For example, the reaction product is washed with an aqueous solution which separates the compound of formula (II) from the starting materials and by-products. In one embodiment the desired product is isolated via distillation.

Exemplary embodiments of the present disclosure are listed below:

Embodiment 1: A method of making a halogenated partially fluorinated compound, the method comprising:
(a) providing a compound having the following structure of formula (I):

R$_f$—CF=CXY wherein X and Y are independently selected from F and Cl; wherein R$_f$ is a fluorinated monovalent group comprising 1 to 10 carbon atoms;

(b) contacting the compound with at least one of
(i) an iodine or bromine containing salt in the presence of an acid; and
(ii) aqueous solution of HZ wherein Z is selected from I and Br to form the halogenated partially fluorinated compound of the formula (II):

R'$_f$—CFH—CXYZ wherein X and Y are independently selected from F and Cl; Z is selected from I and Br; and R'$_f$ is a fluorinated monovalent group comprising 1 to 10 carbon atoms.

Embodiment 2: The method of embodiment 1, wherein R$_f$ comprises at least one catenated oxygen or sulfur atom.

Embodiment 3: The method of any one of the previous embodiments, wherein R$_f$ comprises at least one halogen selected from at least one Cl, Br, and I.

Embodiment 4: The method of any one of the previous embodiments, wherein R$_f$ is a linear, branched or cyclic group.

Embodiment 5: The method of any one of the previous embodiments, wherein R$_f$ is selected from —CF$_2$—O—SO$_2$F; —CF$_2$I; —CF$_2$Br; —O—(CF$_2$)$_a$—F; —O—(CF$_2$)$_a$—I; —O—(CF$_2$)$_a$—Br; —O—(CF$_2$)$_b$—O—CF=XY wherein X and Y are independently selected from F and Cl and a is an integer from 1-10 and b is an integer from 2-4.

Embodiment 6: The method of any one of the previous embodiments, wherein the compound of formula (I) is selected from:
X'—CF$_2$—CF=CF$_2$, CF$_3$—O—CF=CF$_2$, C$_3$F$_7$—O—CF=CF$_2$, CF$_3$CF$_2$CF$_2$—O—CF(CF$_3$)—CF$_2$—O—CF=CF$_2$, X'—(CF$_2$)$_m$—CF=CF$_2$, CF$_3$—O—(CF$_2$)$_3$—O—CF=CF$_2$, CF$_2$=CF—O—(CF$_2$)$_n$—O—CF=CF$_2$, X'—CF$_2$—CF$_2$—O—(CF$_2$)$_m$—O—CF=CF$_2$, CF$_2$=CF—O—(CF$_2$)$_n$—O—CF$_2$—CF=CF$_2$, CF$_2$=CF—CF$_2$—O—(CF$_2$)$_n$—O—CF$_2$—CF=CF$_2$, X'—CF$_2$—CF$_2$—O—(CF$_2$)$_n$—O—CF$_2$CF=CF$_2$, X'—CF$_2$—CF$_2$—O—CF=CF$_2$, X'—CF$_2$—CF$_2$—O—CF$_2$—CF=CF$_2$, X'—CF(CF$_3$)—CF$_2$—O—CF=CF$_2$, X'—CF(CF$_3$)—CF$_2$—O—CF$_2$—CF=CF$_2$, X'—CF$_2$—CF$_2$—(O—CF(CF$_3$)—CF$_2$)$_p$—O—CF=CF$_2$, X'—CF$_2$—CF$_2$—(O—CF(CF$_3$)—CF$_2$)$_p$—O—CF$_2$—CF=CF$_2$, X'—CF$_2$—CF$_2$—CF$_2$—O—CF=CF$_2$, X'—CF$_2$—CF$_2$—CF$_2$—O—CF$_2$—CF=CF$_2$, X'—CF$_2$—CF$_2$—CF$_2$—(O—CF(CF$_3$)—CF$_2$)$_p$—O—CF=CF$_2$, X'—CF$_2$—CF$_2$—CF$_2$—(O—CF(CF$_3$)—CF$_2$)$_p$—O—CF$_2$—CF=CF$_2$, and X'—CF$_2$—CF$_2$—O—(CF$_2$)$_2$—(O—CF(CF$_3$)CF$_2$)$_p$—O—CF$_2$=CF$_2$ wherein X' is selected from Br, I, C(O)X'', and SO$_2$X'' wherein X'' is selected from F, Cl, OH, and salts thereof; m is an integer from 1-4; n is an integer from 2-4; and p is an integer from 1-2.

Embodiment 7: The method of any one of the previous embodiments, wherein R'$_f$ is the same as R$_f$.

Embodiment 8: The method of any one of the previous embodiments, wherein the iodine or bromine containing salt is selected from alkaline halogenides, alkaline earth halogenides, and tetraalkylammonium halogenides.

Embodiment 9: The method of any one of the previous embodiments, wherein the pKa of the acid is at most 4.8.

Embodiment 10: The method of any one of the previous embodiments, wherein the contacting of the compound of formula (I) with the iodine or bromine containing salt occurs in the presence of a solvent.

Embodiment 11: The method of embodiment 10, wherein the solvent is selected from acetonitrile, diglyme, monoglyme, propionitrile, tetraglyme, triglyme, tetrahydrofuran, and water.

Embodiment 12: The method of any one of the previous embodiments, wherein the contacting of the compound with the iodine or bromine containing salt or the aqueous solution of HZ is conducted at a pressure of 1 to 20 bar and a temperature of 20 to 200° C.

Embodiment 13: The method of any one of the previous embodiments, further comprising, (c) reacting the halogenated partially fluorinated compound of formula (II) with a (terminal) hydrocarbon olefin to elongate the halogenated partially fluorinated compound.

Embodiment 14: The method of embodiment 13, further comprising:

reducing the elongated halogenated partially fluorinated compound of embodiment 13 to form a compound of formula (III):

R"—CFH—CF$_2$—CH=CH$_2$ wherein R" is selected from X'—CF$_2$—, CH$_2$=CH—CF$_2$—, CF$_3$O—, CF$_3$CF$_2$CF$_2$—O—, and CF$_3$—O—(CF$_2$)$_3$—O—, wherein X' is selected from Br, I, C(O)X", and SO$_2$X" wherein X" is selected from F, Cl, OH, and salts thereof.

Embodiment 15: A compound having the following structure:
Br—CF$_2$—CFH—CF$_2$—I, CF$_3$—O—CFH—CF$_2$—I, C$_3$F$_7$—O—CFH—CF$_2$—Z, CF$_3$—CF$_2$—CF$_2$—O—CF(CF$_3$)—CF$_2$—O—CFH—CF$_2$—Z, I—(CF$_2$)$_n$—CFH—CF$_2$—I, I—(CF$_2$)$_m$—CFH—CF$_2$—Br, Br—(CF$_2$)$_m$—CFH—CF$_2$—I, Br—(CF$_2$)$_q$—CFH—CF$_2$—Br, CF$_3$—O—(CF$_2$)$_3$—O—CFH—CF$_2$—Z, Z—CF$_2$—CFH—O—(CF$_2$)$_n$—O—CF=CF$_2$, Z—CF$_2$—CFH—O—(CF$_2$)$_n$—O—CFH—CF$_2$—Z, Z—CF$_2$—CFH—O—(CF$_2$)$_n$—O—CF$_2$—CF=CF$_2$, Z—CF$_2$—CFH—O—(CF$_2$)$_n$—O—CF$_2$—CFH—CF$_2$—Z, CF$_2$=CF—O—(CF$_2$)$_n$—O—CF$_2$—CFH—CF$_2$—Z, Z—CF$_2$—CFH—CF$_2$—O—(CF$_2$)$_n$—O—CF$_2$—CF=CF$_2$, Z—CF$_2$—CFH—CF$_2$—O—(CF$_2$)$_n$—O—CF$_2$—CFH—CF$_2$—Z, X'—CF$_2$—CF$_2$—O—(CF$_2$)$_n$—O—CF$_2$CFH—CF$_2$—Z, X'—CF$_2$—CF$_2$—O—CFH—CF$_2$—Z, X'—CF$_2$—CF$_2$—O—CF$_2$—CFH—CF$_2$—Z, X'—CF(CF$_3$)—CF$_2$—O—CFH—CF$_2$—Z, X'—CF(CF$_3$)—CF$_2$—O—CF$_2$—CFH—CF$_2$—Z, X'—CF$_2$—CF$_2$—(O—CF(CF$_3$)—CF$_2$)$_p$—O—CFH—CF$_2$—Z, X'—CF$_2$—CF$_2$—(O—CF(CF$_3$)—CF$_2$)$_p$—O—CF$_2$—CFH—CF$_2$—Z, X'—CF$_2$—CF$_2$—CF$_2$—O—CFH—CF$_2$—Z, X'—CF$_2$—CF$_2$—CF$_2$—(O—CF(CF$_3$)—CF$_2$)$_p$—O—CFH—CF$_2$—Z, X'—CF$_2$—CF$_2$—CF$_2$—(O—CF(CF$_3$)—CF$_2$)$_p$—O—CF$_2$—CFH—CF$_2$—Z, X'—CF$_2$—CF$_2$—O—(CF$_2$)$_2$—(O—CF(CF$_3$)CF$_2$)$_p$—O—CFH—CF$_2$—Z, wherein Z is Br, I; X' is selected from Br, I, C(O)X", and SO$_2$X" wherein X" is selected from F, Cl, OH, and salts thereof; m is an integer from 1-4; n is an integer from 2-4; and p is 1 or 2; and q is 3 or 4.

EXAMPLES

Advantages and embodiments of this disclosure are further illustrated by the following examples, but the particular materials and amounts thereof recited in these examples, as well as other conditions and details, should not be construed to unduly limit this invention. In these examples, all percentages, proportions and ratios are by weight unless otherwise indicated.

All materials are commercially available, for example from Sigma-Aldrich Chemical Company; Milwaukee, Wis., or known to those skilled in the art unless otherwise stated or apparent.

These abbreviations are used in the following examples: b.p.=boiling point, g=gram, h and hr=hour, min=minutes, mol=mole, mbar=millibar, and L=liter.

Example 1

Synthesis of CF$_2$=CF—CF$_2$—I

Perfluoroallylfluorosulfate (CF$_2$=CF—CF$_2$—O—SO$_2$F; 1270 g, 5.5 mol) was added over the course of 9 hrs to a slurry of NaI (531 g, 3.5 mol) and KI (433 g, 2.6 mol) in monoglyme (1910 g) maintained at a temperature between 5 and 20° C. Afterwards, the reaction mixture was poured into H$_2$O (4 L), creating a biphasic material. The organic phase was separated and washed with water, followed by a washing with a 5% solution of Na$_2$S$_2$O$_3$. The organic phase was then distilled, collecting CF$_2$=CF—CF$_2$—I (1246 g, 4.8 mol; b.p. 57° C. at 967 mbar) in an isolated yield of 87%.

Synthesis of I—CF$_2$—CFH—CF$_2$—I

A mixture of acetonitrile (1010 g), trifluoroacetic acid (220 g, 1.9 mol), LiI (511 g, 3.8 mol) and CF$_2$=CF—CF$_2$—I (328 g, 1.3 mol, from above) was heated to 60° C. for 110 hr. Then the reaction mixture was poured into H$_2$O (4 L), creating a biphasic material. The organic phase was separated and washed with water, followed by a washing with a 5% solution of Na$_2$S$_2$O$_3$. The organic phase was then distilled, collecting I—CF$_2$—CFH—CF$_2$—I (402 g, 1.1 mol; b.p. 79° C. at 133 mbar) in an isolated yield of 85%.

Example 2

Synthesis of I—CF$_2$—CFH—CF$_2$—I

In a steel autoclave, a mixture of CF$_2$=CF—CF$_2$—I (7.7 g, 29.9 mmol), [NBu$_4$]I (0.6 g, 1.6 mmol), HI$_{aq}$ (57%; 9.1 mL, 15.5 g, 69.0 mmol) and CH$_3$CN (38.9 g) was heated at 96° C. for 14 hr. Afterwards, the reaction mixture was cooled to 25° C. poured into H$_2$O (50 mL) creating a biphasic material. The organic phase was separated and washed with water, followed by a washing with a 5% solution of Na$_2$S$_2$O$_3$. I—CF$_2$—CFH—CF$_2$—I (2.8 g, 7.8 mmol) was obtained in an isolated yield of 26%.

Example 3

Synthesis I—CF$_2$—CFH—CF$_2$—I

CF$_2$=CF—CF$_2$—OSO$_2$F (300 g, 1.3 mol) was added to a mixture of LiI (455 g, 3.4 mol) and acetonitrile (1010 g) at 10° C. After 6 hr, trifluoroacetic acid (222 g, 1.9 mol) was added at 10° C. and the reaction mixture was intensively stirred and heated up to 60° C. for 106 hr. Subsequently, the reaction mixture was poured into H$_2$O (4 L) creating a biphasic material. The organic phase was separated and washed with water, followed by a washing with a 5% solution of Na$_2$S$_2$O$_3$. The organic phase was then distilled, collecting I—CF$_2$—CFH—CF$_2$—I (77 g, 0.2 mol) in an isolated yield of 15%.

Example 4

Synthesis of $CF_3-O-(CF_2)_3-O-CFH-CF_2-I$ via $HI_{(aq)}$ in a Steel Autoclave In a steel autoclave a mixture of $CF_3-O-(CF_2)_3-O-CF=CF_2$ (10 g, 31.3 mmol), LiI (1.9 g, 14.2 mmol), $HI_{aq}$ (57%; 9.5 mL, 16 g, 72.2 mmol) and $CH_3CN$ (35 g) was heated at 142° C. for 14 h. Afterwards, the reaction mixture was cooled to 25° C. poured into $H_2O$ (50 mL) creating a biphasic material. The organic phase was separated and washed with water, followed by a washing with a 5% solution of $Na_2S_2O_3$. $CF_3-O-(CF_2)_3-O-CFH-CF_2-I$ (6.2 g, 13.5 mmol) was obtained in an isolated yield of 43%.

Example 5:

Synthesis of $I-CF_2-CFH-CF_2-I$

A reaction mixture of acetonitrile (1016 g), acetic acid (114 g, 1.9 mol), LiI (513 g, 3.8 mol) and $CF_2=CF-CF_2-I$ (330 g, 1.3 mol) was heated up to 60° C. for 112 h. Subsequently, the reaction mixture was poured into $H_2O$ (4 L) creating a biphasic material. The organic phase was separated and washed with water, followed by a washing with a 5% solution of $Na_2S_2O_3$. The organic phase was then distilled, collecting $I-CF_2-CFH-CF_2-I$ (251 g, 0.7 mol) in an isolated yield of 54%.

Foreseeable modifications and alterations of this invention will be apparent to those skilled in the art without departing from the scope and spirit of this invention. This invention should not be restricted to the embodiments that are set forth in this application for illustrative purposes.

What is claimed is:

1. A method of making a halogenated partially fluorinated compound, the method comprising:
   (a) providing a compound having the following structure of formula (I):

$R_f-CF=CXY$ wherein X and Y are independently selected from F and Cl; wherein Rf is a fluorinated monovalent group comprising 1 to 10 carbon atoms;
   (b) contacting the compound with at least one of
      (i) an iodine or bromine containing salt in the presence of an acid; and
      (ii) aqueous solution of HZ wherein Z is selected from I and Br to form the halogenated partially fluorinated compound of the formula (II):

$R'_f-CFH-CXYZ$ wherein X and Y are independently selected from F and Cl; Z is selected from I and Br; and $R'_f$ is a fluorinated monovalent group comprising 1 to 10 carbon atoms.

2. The method of claim 1, wherein $R_f$ comprises at least one catenated oxygen or sulfur atom.

3. The method of claim 1, wherein $R_f$ is selected from $-CF_2-O-SO_2F$; $-CF_2I$; $-CF_2Br$; $-O-(CF_2)_a-F$; $-O-(CF_2)_a-I$; $-O-(CF_2)_a-Br$; $-O-(CF_2)_b-O-CF=CXY$ wherein X and Y are independently selected from F and Cl and a is an integer from 1-10 and b is an integer from 2-4.

4. The method of claim 1, wherein the compound of formula (I) is selected from:
$X'-CF_2-CF=CF_2$, $CF_3-O-CF=CF_2$, $C_3F_7-O-CF=CF_2$, $CF_3CF_2CF_2-O-CF(CF_3)-CF_2-O-CF=CF_2$, $X'-(CF_2)_m-CF=CF_2$, $CF_3-O-(CF_2)_3-O-CF=CF_2$, $CF_2=CF-O-(CF_2)_n-O-CF=CF_2$, $X'-CF_2-CF_2-O-(CF_2)_n-O-CF=CF_2$, $CF_2=CF-O-(CF_2)_n-O-CF_2-CF=CF_2$, $CF_2=CF-CF_2-O-(CF_2)_n-O-CF_2-CF=CF_2$, $X'-CF_2-CF_2-O-(CF_2)_n-O-CF_2CF=CF_2$, $X'-CF_2-CF_2-O-CF=CF_2$, $X'-CF_2-CF_2-O-CF_2-CF=CF_2$, $X'-CF(CF_3)-CF_2-O-CF=CF_2$, $X'-CF(CF_3)-CF_2-O-CF_2-CF=CF_2$, $X'-CF_2-CF_2-(O-CF(CF_3)-CF_2)_p-O-CF=CF_2$, $X'-CF_2-CF_2-(O-CF(CF_3)-CF_2)_p-O-CF_2-CF=CF_2$, $X'-CF_2-CF_2-CF_2-O-CF=CF_2$, $X'-CF_2-CF_2-CF_2-O-CF_2-CF=CF_2$, $X'-CF_2-CF_2-CF_2-(O-CF(CF_3)-CF_2)_p-O-CF=CF_2$, $X'-CF_2-CF_2-(O-CF(CF_3)-CF_2)_p-O-CF_2-CF=CF_2$, and $X'-CF_2-CF_2-O-(CF_2)_2-(O-CF(CF_3)CF_2)_p-O-CF_2=CF_2$ wherein X' is selected from Br, I, C(O)X", and $SO_2X"$ wherein X" is selected from F, Cl, OH, and salts thereof; m is an integer from 1-4; n is an integer from 2-4; and p is an integer from 1-2.

5. The method of claim 1, wherein the iodine or bromine containing salt is selected from alkaline halogenides, alkaline earth halogenides, and tetraalkylammonium halogenides.

6. The method of claim 1, wherein the pKa of the acid is at most 4.8.

7. The method of claim 1, wherein the contacting of the compound of formula (I) with the iodine or bromine containing salt occurs in the presence of a solvent.

8. The method of claim 1, wherein the contacting of the compound with the iodine or bromine containing salt or the aqueous solution of HZ is conducted at a pressure of 1 to 20 bar and a temperature of 20 to 200° C.

9. The method of claim 1, further comprising, (c) reacting the halogenated partially fluorinated compound of formula (II) with a (terminal) hydrocarbon olefin to elongate the halogenated partially fluorinated compound.

10. A compound having the following structure:
$CF_3-O-CFH-CF_2-I$, $C_3F_7-O-CFH-CF_2-Z$, $CF_3-CF_2-CF_2-O-CF(CF_3)-CF_2-O-CFH-CF_2-Z$, $CF_3-O-(CF_2)_3-O-CFH-CF_2-Z$, $Z-CF_2-CFH-O-(CF_2)_n-O-CF=CF_2$, $Z-CF_2-CFH-O-(CF_2)_n-O-CFH-CF_2-Z$, $Z-CF_2-CFH-O-(CF_2)_n-O-CF_2-CF=CF_2$, $Z-CF_2-CFH-O-(CF_2)_n-O-CF_2-CFH-CF_2-Z$, $CF_2=CF-O-(CF_2)_n-O-CF_2-CFH-CF_2-Z$, $Z-CF_2-CFH-CF_2-O-(CF_2)_n-O-CF_2-CF=CF_2$, $Z-CF_2-CFH-CF_2-O-(CF_2)_n-O-CF_2-CFH-CF_2-Z$, $X'-CF_2-CF_2-O-(CF_2)_n-O-CF_2CFH-CF_2-Z$, $X'-CF_2-CF_2-O-CFH-CF_2-Z$, $X'-CF_2-CF_2-O-CF_2-CFH-CF_2-Z$, $X'-CF(CF_3)-CF_2-O-CFH-CF_2-Z$, $X'-CF(CF_3)-CF_2-O-CF_2-CFH-CF_2-Z$, $X'-CF_2-CF_2-(O-CF(CF_3)-CF_2)_p-O-CFH-CF_2-Z$, $X'-CF_2-CF_2(O-CF(CF_3)-CF_2)_p-O-CF_2-CFH-CF_2-Z$, $X'-CF_2-CF_2-CF_2-O-CFH-CF_2-Z$, $X'-CF_2-CF_2-CF_2-O-CF_2-CFH-CF_2-Z$, $X'-CF_2-CF_2-CF_2-(O-CF(CF_3)-CF_2)_p-O-CFH-CF_2-Z$, $X'-CF_2-CF_2-CF_2-(O-CF(CF_3)-CF_2)_p-O-CF_2-CFH-CF_2-Z$, $X'-CF_2-CF_2-O-(CF_2)_2-(O-CF(CF_3)CF_2)_p-O-CFH-CF_2-Z$, wherein Z is Br, I; X' is selected from Br, I, C(O)X", and $SO_2X"$ wherein X" is selected from F, Cl, OH, and salts thereof; m is an integer from 1-4; n is an integer from 2-4; and p is 1 or 2; and q is 3 or 4.

11. The method of claim 7, wherein the solvent is optionally selected from acetonitrile, diglyme, monoglyme, propionitrile, tetraglyme, triglyme, tetrahydrofuran, and water.

12. The method of claim 1, wherein $R_f$ comprises at least one halogen selected from at least one Cl, Br, and I.

13. The method of claim 1, wherein $R_f$ is a linear, branched or cyclic group.

14. The method of claim 1, wherein $R'_f$ is the same as $R_f$.

15. The method of claim 9, further comprising:
reducing the elongated halogenated partially fluorinated compound of claim 9 to form a compound of formula (III):

R"—CFH—CF$_2$—CH=CH$_2$ wherein R" is selected from X'—CF$_2$—, CH$_2$=CH—CF$_2$—, CF$_3$O—, CF$_3$CF$_2$CF$_2$—O—, and CF$_3$—O—(CF$_2$)$_3$—O—, wherein X' is selected from Br, I, C(O)X", and SO$_2$X" wherein X" is selected from F, Cl, OH, and salts thereof.

* * * * *

UNITED STATES PATENT AND TRADEMARK OFFICE
CERTIFICATE OF CORRECTION

PATENT NO. : 10,099,982 B2
APPLICATION NO. : 15/529116
DATED : October 16, 2018
INVENTOR(S) : Klaus Hintzer et al.

It is certified that error appears in the above-identified patent and that said Letters Patent is hereby corrected as shown below:

In the Specification

Column 1,
Line 4, delete "REFERECE" and insert -- REFERENCE --, therefor.
Line 5, delete "APPLICTIONS" and insert -- APPLICATIONS --, therefor.

Column 2,
Line 67, after "thereof." insert -- Exemplary salts of C(O)OH include for example, ammonium salts, alkali and alkaline earth metal salts, such as C(O)ONa. --.

Column 3,
Lines 51 & 52, delete "terabutylammonium," and insert -- tetrabutylammonium, --, therefor.

Column 4,
Line 53, delete "Z=I," and insert -- Z=I, --, therefor.
Line 62, delete "Z=I," and insert -- Z=I, --, therefor.

Column 5,
Line 21, delete "thereof" and insert -- thereof. --, therefor.

Column 6,
Line 36, delete "—(CF$_2$)$_m$—" and insert -- —(CF$_2$)$_n$— --, therefor.

In the Claims

Column 9,
Line 43, in Claim 1, delete "Rf" and insert -- R$_f$ --, therefor.

Column 10,
Line 37, in Claim 9, delete "(c)" and insert -- (b) --, therefor.

Signed and Sealed this
Nineteenth Day of February, 2019

Andrei Iancu
*Director of the United States Patent and Trademark Office*